United States Patent [19]
D'Urso

[11] Patent Number: 5,752,962
[45] Date of Patent: May 19, 1998

[54] SURGICAL PROCEDURES

[76] Inventor: Paul S. D'Urso, 30 Pelham Street, Coorparoo, Queensland 4151, Australia

[21] Appl. No.: 646,320

[22] PCT Filed: Oct. 13, 1994

[86] PCT No.: PCT/AU94/00626

§ 371 Date: Jul. 15, 1996

§ 102(e) Date: Jul. 15, 1996

[87] PCT Pub. No.: WO95/13758

PCT Pub. Date: May 26, 1995

[30] Foreign Application Priority Data

Nov. 15, 1993 [AU] Australia ............... PM 2398

[51] Int. Cl.⁶ .................................................. A61B 19/00
[52] U.S. Cl. .................................. 606/130; 128/857
[58] Field of Search ........................ 128/845, 846, 128/857, 858; 606/130, 167

[56] References Cited

U.S. PATENT DOCUMENTS

| | | | |
|---|---|---|---|
| 4,228,799 | 10/1980 | Anichkov | 606/130 |
| 4,230,117 | 10/1980 | Anichkov | 606/130 |
| 4,436,684 | 3/1984 | White | 606/130 |
| 4,613,324 | 9/1986 | Ghajar | 606/130 |
| 5,205,289 | 4/1993 | Hardy | 606/130 |
| 5,280,427 | 1/1994 | Magnusson | 606/130 |
| 5,387,220 | 2/1995 | Pishurodi | 606/130 |

*Primary Examiner*—Michael A. Brown
*Attorney, Agent, or Firm*—Madson & Metcalf

[57] ABSTRACT

A method for stereotactic surgical procedure including securing to a predetermined region of anatomy of a patient, at least two stereotaxy frame attachment device. Tomographically scanning the predetermined region to generate scanning data relating to internal and external surfaces of the anatomical region including the frame attachment device and inputting into a data storage device the scanning data.

18 Claims, 4 Drawing Sheets

SURGICAL PROCEDURES

This invention is concerned with a method and apparatus for carrying out surgical procedures.

The invention is particularly concerned with the use of stereolithographic models constructed from tomographic data as a pre-operative aid in carrying out the surgical procedure and as a post-operative aid in monitoring a treated patient.

Modelling of anatomical regions using computed tomography data is well known for pre-operative planning and rehearsal of procedures and in the manufacture of prosthetic devices.

These modelling techniques employ digitised information from CAD-CAM design systems based on data captured and/or reconstructed from a variety of reflection and/or transmission scanning devices. Typically, such scanning device include X-Ray, magnetic resonance imaging (MRI), magnetic resonance angiography (MRA), position emission tomography (PET) as well as ultrasonic imaging.

U.S. Pat. Nos. 4,436,684 and 4,976,737 describe the construction, by mechanical means of anatomical models from computed tomography data.

Of more recent times, stereolithographic modelling has gained prominence due to its ability to create highly accurate anatomical models replicating both internal and external features of a region under consideration. In particular, stereolithographically reproduced models have been used to permit pre-planning of surgical procedures and, in the case of plastic and reconstructive cranial surgery in particular, some degree of rehearsal of surgical procedures is possible.

Stereolithographic and other modelling processes are described in "Paediatric craniofacial surgery: Comparison of milling and stereolithography for 3D model manufacturing *Pediatr. Radiol.* (1992) 22: 458:460; "Computer-Aided Simulation, Analysis and Design in Orthopaedic Surgery", *Orthopaedic Clinics of North America*—Vol 17, No. 4, October 1986; and "Solid models for CT/MR image display: accuracy and utility in surgical planning", Vol 1444 Image Capture, Formatting and Display (1991): 2–8.

Generally speaking, stereolithographic modelling is employed mostly in the construction of models corresponding to bony tissue although with MRI tomography high resolution imaging of soft tissue has permitted reconstruction of three dimensional images of soft tissue organs for display on monitors. Such displays permit pre-operative planning and monitoring during surgical procedures such as biopsy sampling, radiotherapy implantation etc. A method of manufacturing stereolithographic models from computed tomography data is described in International Patent Application No. PCT/AU94/00536.

In many surgical procedures, particularly intracranial procedures, there is a need for precise location of soft tissue masses such as malignant lesions, tumours etc relative to other organs such as blood vessels and neural pathways to facilitate pre-operative planning to minimise the risk of accidental trauma to adjacent organs.

One technique for pre-operative planning employs a stereolithographic model of a cranial structure in combination with computed tomography data displayed on a viewing screen. This enables a surgeon to spatially visualise the three dimensional spatial juxtaposition of soft tissue masses within a cranial cavity and relative to structural features thereof.

While this technique is a significant improvement over the mental analysis of two dimensionally displayed reconstructions of three dimensional images, there remains an element of "guesswork" in mental spatial translation of two dimensional images to three dimensional space.

Another procedure involves the use of a stereotactic frame associated with a patients anatomy as a fixed reference datum in combination with computed tomography data to precisely spatially locate selected regions of soft tissue mass.

Stereotaxis procedures are described in "Guided Microsurgery by Computer-Assisted Three-Dimensional Analysis of Neuroanatomical Data Stereotactially Acquired", *Stereotact. Funct. Neurosurg.* 1990: 54455: 482–487; "Three-Dimensional Reconstruction of Neuroradiological Data within a Stereotactic Frame of Reference for Surgery of Visible Targets", *Appl. Neuro.* 50:77–80 (1987); "The Computer and Stereotactic Surgery in Neurological Surgery", *Comp. Med. Imag. and Graphics*, Vol 12, No. 1 pp75–83 (1988); and, "Integrated Stereotaxis Imaging with CT, MR Imaging, and Digital Subtraction Angiography", *Radiology* 1986; 161:821–826.

Stereotaxis surgery is widely used for aspiration and biopsy of intracranial lesions; implantation of electrodes for sub-cortical stimulation and for the location of seizure foci, thalamotomy for movement; pain and effective disorders; definition of tumour volume for laser vaporisation; and external beam or interstitial irradiation.

Computed tomography imaging techniques employing X-Ray irradiation are inherently free of geometric distortion and offer good differentiation between soft and bony tissues although there are some limitations in resolving soft tissue boundaries where the soft tissues have x-ray attenuation coefficients that differ by less than about 0.5%.

Magnetic Resonance (MR) imaging is free of bone artefact and gives excellent anatomical detail. Stereotaxy involving MR imaging however requires the use of an attachable frame which does not interact with the imaging process. In consequence such frames suitable for MR imaging are constructed from quite exotic materials and are very expensive.

In use, stereotaxy frames are fixed to a patient's skull under a general anaesthetic by means of carbon fibre or aluminium pins in drill holes in the skull. Locking members retain the pins in place. The frame is then attached to the pins by locking collars and the patient is then subjected to an imaging process.

During the imaging process accurate location of the imaged section within the frame is accomplished by marker sets to establish x, y and z coordinates within the spatial volume of the frame. Using appropriate computer software, the precise spatial location of a tissue mass relative to the frame coordinates permits distance and angular measurements and plotting of probe trajectories.

While very effective in surgical procedures, there are a number of disadvantages associated with these stereotaxis techniques.

One disadvantage is the need for prolonged anaesthesia whilst a patient undergoes figment of the stereotactic frame, image scanning and then a surgical procedure, although it is possible to disconnect the frame after imaging and accurately refit it to the mounting pins if a delay between imaging and surgery occurs.

Another difficulty is the highly technical nature of the procedure which is dependent upon specialised computer software and hardware as well as experienced computer operators. The highly technical nature of the computer system can act as a disincentive for many surgeons untrained in computer technology or otherwise who are intimidated by computer technology.

A separation of skills between a surgeon and a computer technician in surgical procedures is highly undesirable in stereotaxy as a complete awareness of some anomaly such as mirroring of images may not be apparent to both parties involved in the procedure.

Accordingly, there is a need for a simple yet thoroughly reliable stereotactic technique which is not dependent on computation of data and visual analysis of two dimensional images for verification of the computed data.

It is an aim of the present invention to provide a simple yet reliable stereotactic procedure using a reconstructed three dimensional model to check computed data relating to spatial coordinates within the frame or otherwise to utilise the model to set up a stereotactic frame for surgical procedures.

According to one aspect of the invention there is provided a method for stereotactic surgical procedures comprising the steps of:

- securing, to a predetermined region of anatomy of a patient, at least two stereotaxy frame attachment means;
- tomographically scanning said predetermined region to generate scanning data relating to internal and/or external surfaces of said anatomical region including said frame attachment means and inputting into a data storage means said scanning data;
- computing said scanning data according to a predetermined algorithm to generate a three dimensional coordinate data set for the anatomical region;
- generating from said three dimensional coordinate data set an anatomical replica of selected portions of said anatomical region including said frame attachment means;
- attaching to replicated frame attachment means on said anatomical replica a stereotaxy frame and aligning instrument support means associated with said frame for carrying out a predetermined surgical procedure on a selected portion of anatomical region represented by a replication of said selected portions; and
- securing said stereotaxy frame to said at least two attachment means associated with said predetermined anatomical region of said patient and performing a surgical procedure on said selected portion of said anatomical region with pre-aligned instruments supported on said instrument support means.

Preferably said frame attachment means are comprised of a material detectable by tomography scanning apparatus but otherwise do not interfere with image data produced thereby.

Suitably, said attachment means comprise non-magnetic material.

If required the attachment means comprise metallic or non metallic elements such as ceramics, carbon fibre, plastics, aluminium and the like.

The attachment means may comprise pins, plugs, sockets, spigots, clamps or any other suitable means for releasable attachment of a stereotaxy frame to an anatomical region in a spatially reproducible manner.

The attachment means may comprise one or more attachment elements.

Preferably the attachment means comprises at least two attachment elements.

The attachment means may comprise identical or non identical elements. Tomographic scanning may be carried out with any suitable means for generation of scanning data.

Suitably tomographic scanning is unimodal.

If required tomographic scanning may be multi-modal to generate a plurality of separate scanning data sets and/or combined scanning data sets.

The stereotaxy frame may comprise manually operable instrument alignment means. Alternatively, the stereotaxy frame may comprise mechanical or electro-mechanical instrument alignment means for automated or semi-automated alignment and/or manipulation of instruments associated therewith.

The anatomical replica produced from scanning data may be produced by any suitable means, preferably by stereolithographic modelling.

According to another aspect of the invention there is provided a stereotaxy frame comprising:

- a base member having at least two spaced apertures for attachment to a region of anatomical pathology and/or a replicated region of anatomical pathology; and,
- an instrument support means adapted to align a trajectory of said instrument according to a selected set of spatial coordinates.

If required the base member may comprise two or more leg members, each having an attachment aperture at a free end thereof.

Suitably the instrument support means is pivotally associated with said base member.

Preferably said instrument support means comprises locking means to releasably secure said support means relative to said base member.

The instrument support means may be pivotally associated with said base member by a ball and socket joint.

Alternatively the base member may comprise a contoured member having a support surface complementary to a selected region of anatomical pathology and a tubular instrument support means fixed relative thereto.

Suitably the contoured member comprises a moulded plastics member having a tubular instrument guide encapsulated therein.

If required the contoured member may include a plurality of tubular instrument guides.

In order that the invention may be fully understood and put into practical effect, reference will now be made to various preferred embodiments illustrated in the accompanying drawings in which.

A patient is prepared initially for image scanning for, say, an intra-cranial lesion for preoperative planning of a biopsy and/or aspiration thereof.

Figure 1:
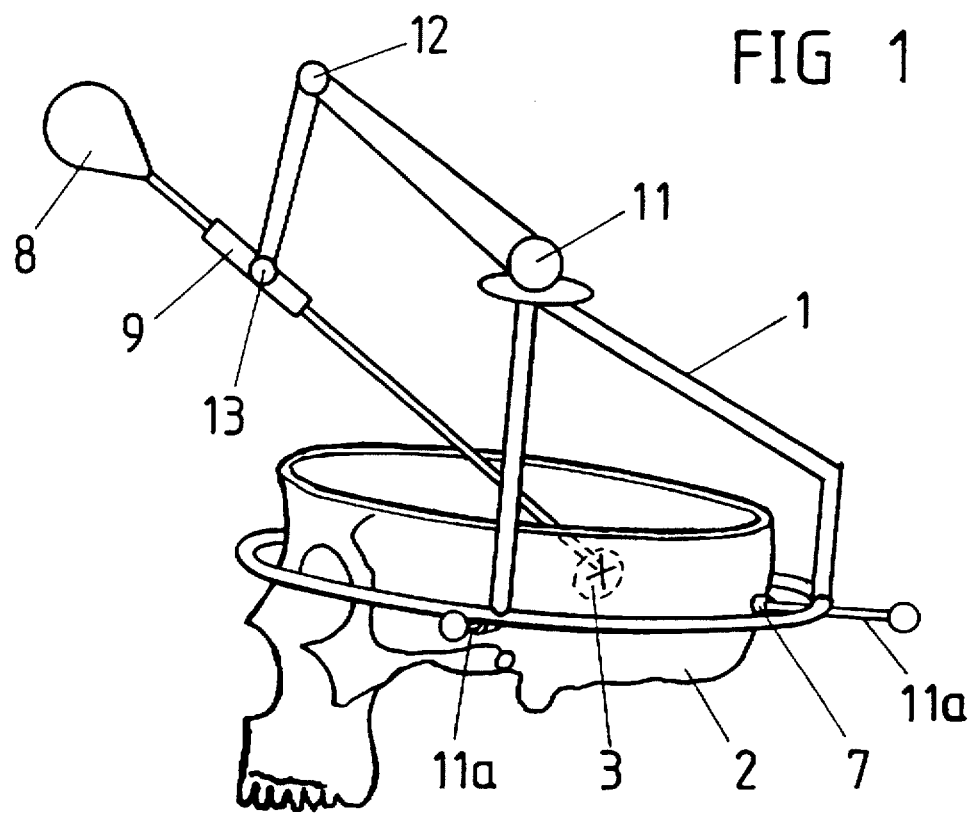
FIG. 1 shows a side view of a stereotaxy frame in association with a stereolithographic model.

Before scanning is effected a stereotaxy frame 1 shown generally in FIG. 1 is attached to the patient's skull under a general or local anaesthetic by means of ceramic, carbon fibre or aluminium pins (not shown) located in blind bore holes in the patient's skull. The stereotaxy frame is then removed from the patient's skull.

The patient is then able to undergo image scanning by say magnetic resonance imaging (MRI) or magnetic resonance angiography (MRA) without the stereotaxy frame which may interfere with the imaging process or otherwise give rise to geometric distortions which cannot be corrected for in computation of the scanning data to recreate two dimensional and three dimensional images.

The scanning process may utilise a single scanning mode (e.g. MRI) to generate data or it may be multi-modal (e.g. x-ray CT and MRI) to create separate or combined images of bony tissue and soft tissue.

After computing the scanning data to obtain reconstructed image data corresponding to the anatomical region, the image or image data may then be edited using known graphics editing techniques to exclude extraneous tissue regions. For example, the outer bony contours of the skull in the region of interest are retained as is the lesion soft tissue boundaries. Adjacent vascular structures may also be retained and if access to the lesion is necessitated via intracranial bone, this structure may also be retained.

The edited image data is then reconstructed by appropriate computer software to generate three dimensional coordinate data for the skull region of interest including the stereotactic frame mount images and internal soft and bony structures of interest.

Figure 2:
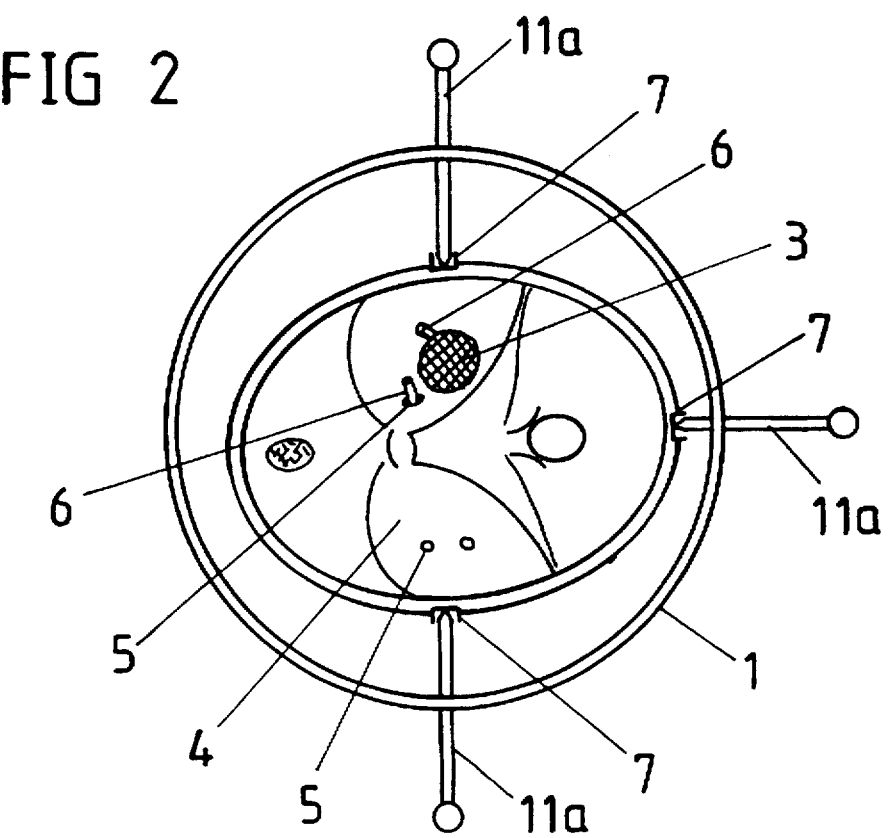
FIG. 2 shows a plan view of the arrangement of FIG. 1.

Utilising the three dimensional coordinate data, a stereolithographic replica 2 of the anatomical pathology is constructed as shown in FIGS. 1 and 2. From this replica the surgeon is able to readily determine the shape and size of the lesion 3 and its spatial relationship to intracranial bone plates 4, neurovascular apertures 5 and blood vessels 6.

By direct visual inspection of a substantially exact replica of the anatomical region of interest a surgeon is able to carry out a non invasive "examination" of lesion 3 and determine with precision its spatial relationship with anatomical features without having to use his imagination to mentally reconstruct two or three dimensional images displayed two dimensionally on a computer monitor.

This direct visual examination permits pre-operative planning to accurately determine the trajectory and depth of penetration of a surgical instrument to minimise trauma along the trajectory path and to avoid damage to blood vessels, nerves and other organs adjacent the lesion site. Where it is necessary to penetrate a bone plate 4 for access to lesion 3, the surgeon can directly measure the bone thickness at the penetration site and also determine whether or not a sinus passage exists in the region.

Stereotactic frame 1 is then secured to the replica via replicated attachment sockets 7 and a surgical instrument 8, supported in a guide 9 on an articulated arm 10, is then aligned with the lesion 3 along a suitable trajectory. The pivotal joints 11, 12, 13 of arm 10 are clamped to prevent movement or, by means of graduated markings, are able to be accurately repositioned in a predetermined trajectory after movement.

The surgeon may then practice the surgical procedure on the replicated model whilst being able to visual examine the effects of the procedure.

When the surgeon is ready to carry out the procedure on the patient, the patient is prepared for theatre, anaesthetised and frame 1 is refitted to the attachment sockets fitted to the patient's skull. By employing sockets or other fittings having differing shapes and/or sizes, the stereotactic frame may only be refitted to the patient's skull in one position. Screw threaded frame mounting rods 11a also include markings or graduations to ensure a precise relocation of the frame on the patients skull.

The surgical procedure may now be carried out on the patient in an otherwise conventional manner via a small hole drilled in the patient's skull. The pre-aligned or re-aligned instrument guide 9 then permits the surgeon to insert instrument 8 into a patient's skull with considerable confidence as the "guesswork" associated with conventional procedures has been eliminated as has the risk of computational error in calculating trajectories from scanning data.

Figure 3:
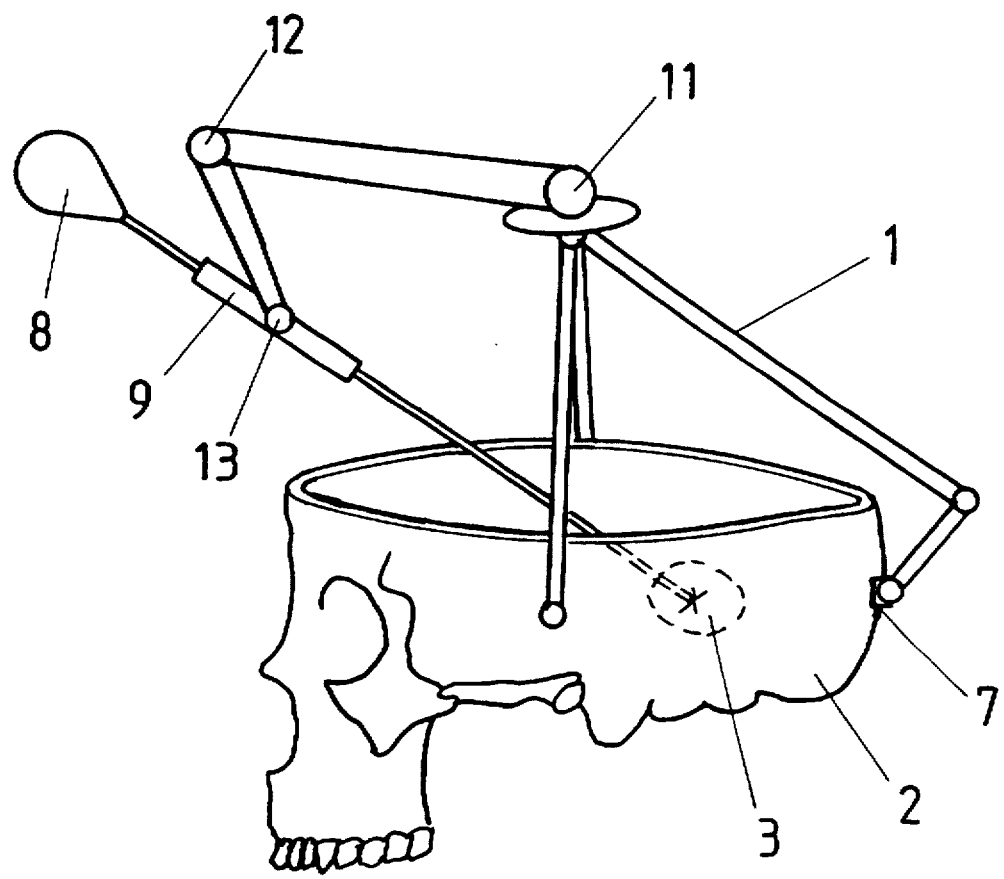
FIG. 3 shows a side view of an alternative embodiment of a stereotaxy frame.

FIG. 3 shows an alternative stereotactic frame assembly suitable for the method according to the invention.

In this embodiment a tripod-like frame attaches directly to frame mounting means whereas the embodiment of FIG. 1 comprises a tripod-like frame attached to a ring frame which in turn attaches to the frame mounting means.

Figure 4:
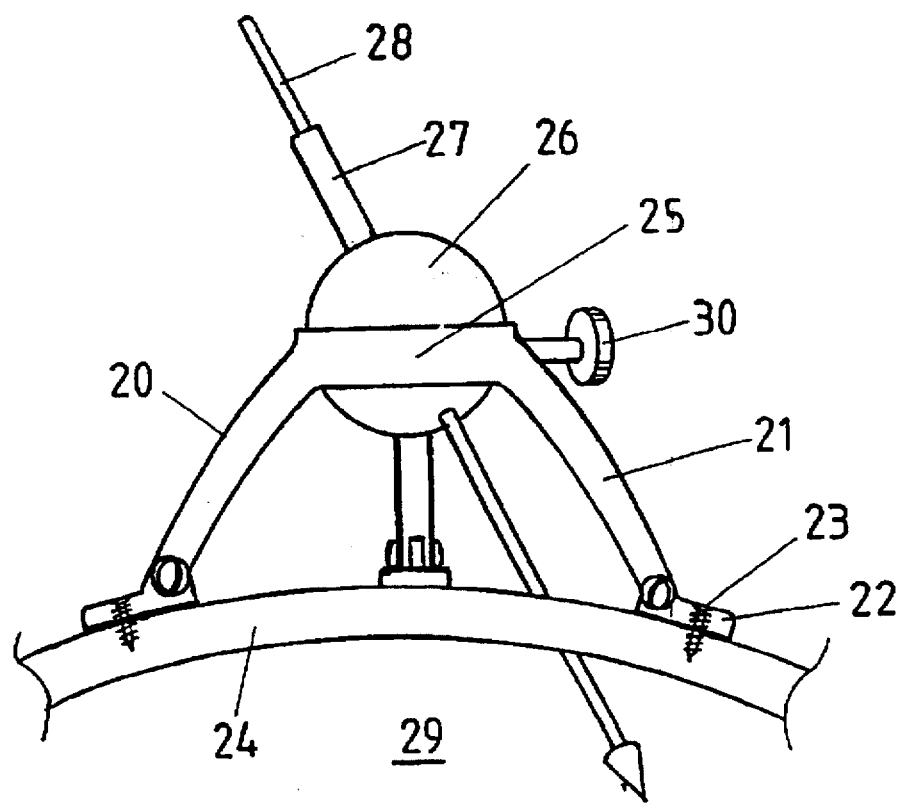
FIG. 4 shows yet another embodiment of a stereotaxy frame.

FIG. 4 shows yet another form of stereotaxy frame according to the invention.

In FIG. 4 the frame comprises a base member 20 having tripod legs 21 extending therefrom. Adjustable feet 22 are provided at the free end of legs 21, the feet 22 having mounting apertures 23 therein for attachment to a region of anatomical pathology 24.

Mounted in a part spherical socket 25 atop legs 21 is a spherical instrument support member 26 adapted for pivotal movement within socket 25.

Located within support member 26 is a guide tube 27 to guide instrument 28 along a predetermined trajectory into the intracranial region 29.

A locking screw 30 is mounted in socket 25 to lock the support member 26 in a predetermined position.

Figure 5:
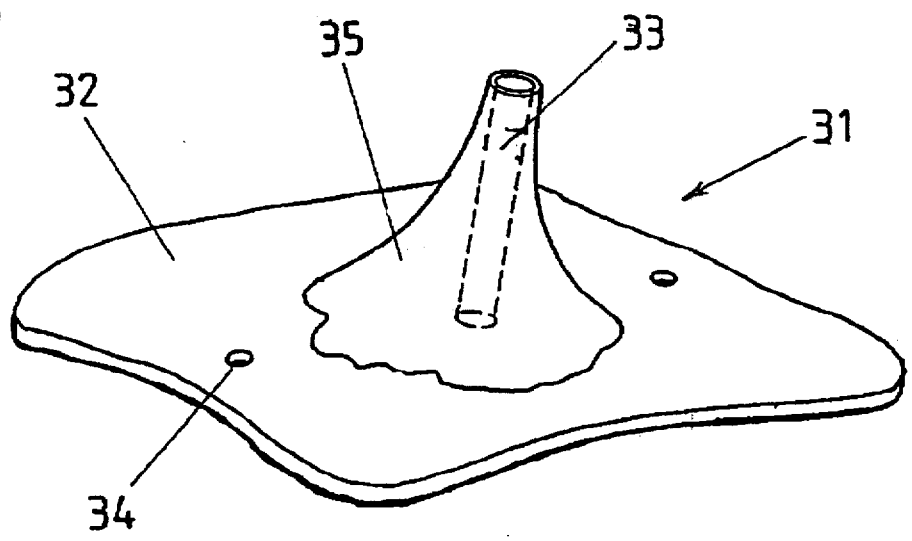
FIG. 5 shows a further embodiment of a stereotaxy frame.

FIG. 5 shows a further embodiment of a stereotaxy frame or template 31.

Template 31 may be fabricated by forming a contoured template base 32 from scan data to form a stereolithographic analogue (SLA) model of a predetermined region of anatomical pathology of interest.

The template outline may be utilised as a peripheral resection template or it may be used as a base to support a guide tube 33 for a surgical instrument.

After template 31 is formed with reference apertures 34 from a patient's scan data, the template is secured to the region of interest on the SLA model using the replicated reference mounting points. A hole is drilled through the template and through the SLA model thereunder to permit insertion of a surgical instrument (not shown).

When the desired trajectory of the instrument is determined from a probe through the SLA model, a guide tube 33 is slipped over the top of the instrument shaft to locate on the surface of the template but otherwise aligned with the longitudinal axis of the instrument. A curable resin dough or putty of polyester, acrylic resin or the like 35 is then formed around the tube 33 to secure the tube 33 in the desired alignment relative to template 31.

The template 31 with aligned guide tube 33 is then transferred to the patient and secured to the patient via screws or the like (not shown) extending through apertures 34.

A drill bit may then be inserted through tube 33 to form an aperture in a bony anatomical pathology such as a skull and a surgical instrument may then be guided to a predetermined depth into the intracranial cavity along a trajectory predetermined by the "practice" alignment on the SLA model.

Figure 6:
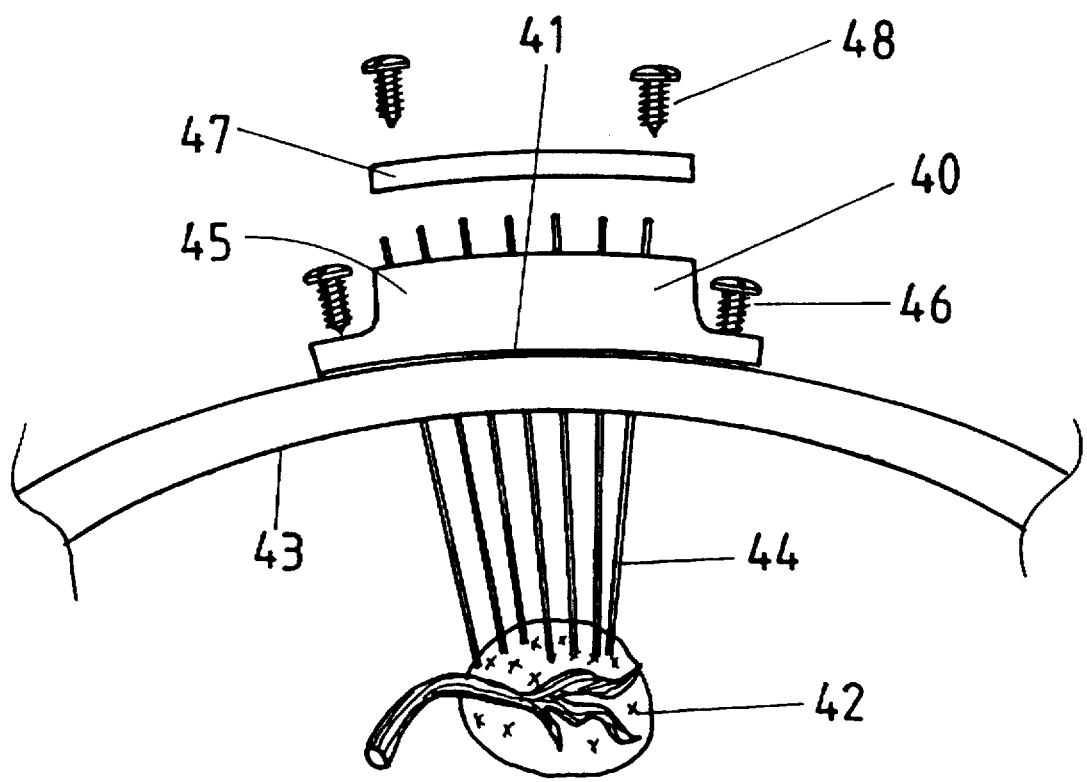
FIG. 6 shows a stereotaxy frame adapted for bracytherapy procedures.

FIG. 6 shows a practical application of another aspect of the invention to bracytherapy procedures.

A template 40 is modeled using patient scan data to ensure a complementary mounting surface 41 with a patient's anatomical pathology.

The precise location of a tumour or the like 42 is located relative to the surface contour of bony mass 43 and a plurality of treatment rods 44 are inserted through drilled apertures in the base of template 40 and bony mass 43. Guide tubes (not shown) are then slipped over the free ends of rods 44 to locate within a cavity (not shown) in the body 45 of template 40. A castable resin (not shown) then secures the guide tubes within the body 45 in relative angular relationship to guide the rods 44 to a predetermined position in the replicated tumour 42.

At the same time, the ends of rods 44 are trimmed or otherwise fitted with depth stops to ensure a controlled insertion depth.

The template 40, secured to the SLA model is then removed by removing screws 46 and is secured to the patient's skull at the reference points replicated on the SLA model, again by means of screws 46.

The guide tubes (not shown) secured in the body of template 40 then permit the drilling of accurately aligned holes in the patient's skull and subsequent insertion of the rods 44 having radiotherapeutic tips along a predetermined trajectory to a predetermined depth to penetrate the tumour 42.

A removable cap 41 is attached to the template body 45 by means of screws 48 to retain rods 44 at their initially inserted depth and otherwise to form a hygienic closure. The removable cap 46 permits the rods 44 to be changed at periodic intervals with a minimum of trauma to the patient.

Figure 7:
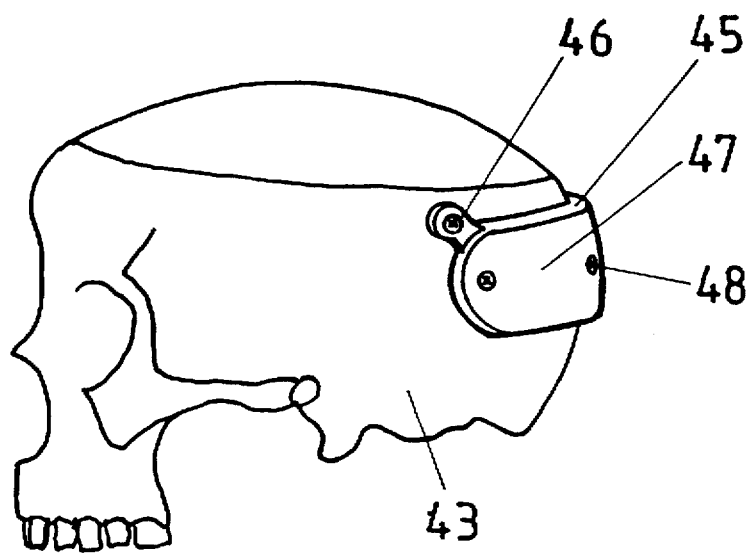
FIG. 7 shows the fitting of the frame of FIG. 6 to a skull region.

FIG. 7 shows schematically the fixture of template 40 to the body skull structure 43 of a patient.

EXPERIMENTAL DATA

Several techniques of model guided stereotaxic surgery were developed. Two techniques were firstly investigated as a phantom experiment and then two similar techniques were carried out on patients.

PHANTOM STUDIES

A cadaveric skull with phantom plaster tumours was marked at four points 2 mm holes and CT scanned in a water bath. CT scanning was on a G.E. 9800. (General Electric Medical Systems, Milwaukee, U.S.A.).

Images were obtained in bone algorithms 1.5 mm thick and in 1.5 mm contiguous increments. The data was loaded in a Silicon Graphics computer work station which runs ANALYZE v 6.2 3D software (Biomedical Imaging Resource, Mayo Foundation, Rochester U.S.A.) 3D reconstruction of the data performed and the anatomy of interest is edited. BRIDGEWORKS software (Solid Concepts California) is used to generate a support file.

SLA model production occurs as a laser selectively polymerises 0.25 mm slices of photo-sensitive monomer upon a platform that is suspended and progressively lowered by 0.25 mm into a vat of the liquid monomer as each slice is polymerised. The SLA model is built up by these contour slices fused one on top of each other. SLA model production time is dependent primarily on the number of slices required for fabrication, the mean time being about 16 hours. The model is then cleaned of support structure and hardened in an ultra violet oven.

The SLA model produced was fitted with a stereotaxic frame by way of the four marker holes. Coordinates for ten "tumour" landmarks were taken on three occasions. The frame was transferred to the cadaveric skull and the ten co-ordinates identified on three occasions. The distance of the pointer tip from the target was recorded.

A second form of stereotaxic surgery was also investigated using the cadaveric skull and SLA model. A custom made template may also act as a guide for instruments so as to perform intracranial operations. One or multiple intracranial trajectories may be chosen and incorporated into the template by means of barrels. Such a template is made to localise two marker points and fit the external contour of the SLA model.

A template was made to fit the phantom SLA model to localise one of the phantom tumours with a wire pointer. Two screws were used to fasten the template to the marker holes found on both cadaveric skull and SLA model. The template was then transferred to the cadaveric skull the screws fastened to the marker holes and the pointer was used to localise the tumour.

PATIENT STUDIES

Two patients requiring resection of skull based tumours where the resection would leave a cranial defect were selected. The biomodelling procedure was identical to the phantom study except that the patient was tattooed with Indian ink at four points and E-Z MARK CT markers were applied at these tattoos.

SLA models were used to prepare custom acrylic custom implants. The master implant may be made from wax or an anatomical section of the normal side may be mirrored or interpolated to fit the defect. The mast implant is then hand finished and used to mould and cast an acrylic custom implant.

CASE 1

A custom made stereotaxtic template may also be made to fit an operative plan on an SLA model so that it traces out a resection margin drawn on the SLA model by the surgeon allowing the insertion of a prefabricated implant. A patient with a large tempero-occipital Tumour was selected. The surgeon marked out the resection margin on the SLA model and acrylic was moulded so that the edges fitted perfectly into the margin and incorporated the two marker points as two holes. The resection was rehearsed and the SLA model was used to prepare a customised implant as previously described.

The surgeon places the template over the scalp and localises the two tattoos and is held firmly whilst a drill is used to make marker holes in the skull cortex. A scalp flap is then reflected. The template was then fixed over an exposed menigioma involving the external temporal region using the two markers and its contour. The resection margin was traced from the boundary of the template. The tumour was then resected. The implant fitted to within—1.5 mm.

CASE 2

A stereotaxic frame was used to localise a lytic tumour in the sphenoidal region of a patient. The surgeon marked the ideal resection margin out on the SLA mode. The model was located in stereotaxic frame according to four marker points. Co ordinates were taken form the margin on the SLA model.

The patient was prepared intraoperatively for stereotaxic surgery. The tattoo marks were identified on the patient's scalp and used to orientate the stereotaxic frame. The patients scalp was reflected and the frame used to replicate the co ordinates of the SLA model resection margin.

The margin varied by—4 mm from that on the SLA model. Due to this inaccuracy the implant was used as a template for resection and was matched to the surface contour of the patients spinode and had its boundary marked to replicate the margin on the SLA model. After resection the implant was accurately inserted. Inaccuracy beyond that in the phantom study was due to soft tissue movement during the application of the stereotaxic frame.

RESULTS

PHANTOM

The accuracy of localisation was—10.25 mm (mean of thirty localisation's) with the stereotaxic frame. Inaccuracy was mainly due to the +0.85 mm size discrepancy of the SLA model. The use of the template in the phantom study was within <0.75 mm and was far simpler to perform for a single point.

PATIENTS

These finding were also reflected in the operating theatre with the two patients. The frame transfer technique had an inaccuracy up to 4 mm whilst the template transfer was <1.5 mm. The template was found to be more simple to apply than the frame which because of its cumbersome size resulted in some soft tissue movement during application which magnified the degree of error to 4 mm.

CONCLUSIONS

The transfer device for model assisted stereotaxic surgery may take several forms, each with its own merits.

1. A simple impression template may be produced. For example, a moulded plastic could be used to race out a boundary or to guide an intracranial trajectory. Such a template could be fabricated on the SLA model and then transferred to the patient and aligned by the matching of contours. This is a simple device may be difficult to localise if the contour is not sufficiently distinctive. Attachment of marker pins or screws will however overcome this problem as these markers are accurately reproduced on the SLA model.
2. The surface markers can be used to precisely locate the transfer device which may take the form of a frame or template.

A customised template may be located to both contour and at least two markers and be used to race a boundary for a craniotomy so that a customised acrylic plate can be used to close the defect after resection. A customised template is located to marker points on the SLA model. One or multiple intracranial trajectories may then be chosen and incorporated into the template by means of a barrel. This technique has special application in bracytherapy. A customised template may be made so that the implants may be encased within the template by means of a lid with screws. Such a device can be made to allow the patient to move about within the ward easily.

The technique may also be carried out using any standard stereotaxic frame as described. The accuracy of the procedures was comparable to the presently described stereotaxic techniques. The great source of error in the phantom study was due to the relative oversize inaccuracy of the SLA model by—0.85 mm. This problem may be solved by improving the CT resolution to a spiral generated 512×512 image matrix incorporating a scaling factor to improve SLA model accuracy. Other sources of error were apparent in the patient study. These were: soft tissue movement and the cumbersome nature of the standard stereotaxic frame. Soft tissue movement can be minimised by reflecting the scalp for template attachment and by using marker pins for the transfer device to lock onto.

Stereotaxy frames according to the invention will be found in practice to be ergonomically efficient and simple to use. The device are ergonomic in the surgical practice to the model guided stereotaxic surgery. One device has three point attachment and a base diameter of 10 cm. (see diagram) A ball in socket instrument guide would allow a wide trajectory angle and adjustable feet for easy surface attachment. This device is re-useable and would be compatible with marked SLA models.

The patient is examined by the surgeon and the best position of frame is determined using standard imaging data or similar SLA models. The frame is then held against the patients head and the scalp where the frames feet rest is shave and infiltrated with local anaesthetic.

The frame is held firmly against the patients head and is used to guide the insertion of three marker points into the bone cortex. The frame is then removed and the patient undergoes CT/Mr scanning.

An SLA model is created and the frame is attached to the marker points incorporated in the model. The trajectory of the procedure is determined and the frame is locked. The locked frame is then transferred to the patients hepo and attached to the marker points. This the acts firstly as a drill guide to breach the patients cranium and then as a guide for the procedure. The frame can be used easily for multiple trajectory transfer from model to patient, for multiple biopsies or for marking a pre planned resection margin.

These new techniques of model assisted stereotaxic surgery have advantages over presently used method for the following reasons:

(a) Being a simple transfer system the skills needed by the surgeon are mechanical and similar to those required for standard operations so little training is necessary. No computer or computations are necessary to implement these techniques in the operating theatre as the technology is hidden in the creation of the exact SLA model.

(b) The frames are simple, cheap and resuable and the only system cost for the hospital. The models are made on a case by case basis.

(c) The patient can be scanned without the frame several days before the procedure.

(d) Conventional "slice" images of CT/MR data are complex and require subjective reconstruction to attain three dimensional understanding. The accuracy of such reconstruction is dependent upon the experience and spatial aptitude of the observer. Realistic accurate SLA models provide a readily recognisable solid replica of a person's anatomy that requires no mental reconstruction.

(e) SLA models optimise pre-operative surgical planning and rehearsal because a solid anatomical replica may be used realistically and interactively to simulate surgery e.g. a sterotaxic trajectory. This allows the surgeon to plan modification to standard techniques and view the planned result.

(f) SLA models provide patients with a clearer understanding of their pathology and the aims and limitations of surgery pre-operatively and improve informed consent.

(g) SLA models require no specialised equipment or knowledge for interpretation and use, are rugged, and may easily be transported and sterilised for intra-operative use.

The study has been carried out at low cost with relatively simple materials. Advances in SLA biomodelling technology will produce models with near perfect accuracy, coloured soft tissue, blood vessels and bone, at low cost. These advances will allow superior results from model guided sterotaxic surgery in future.

While the invention has been described with reference to an intracranial surgical procedure, it should be understood that the method may be adapted to a wide variety of surgical procedures such as joint replacements and delicate procedures such as prostatectomies involving less invasive procedures than hitherto.

In particular it is believed that the method according to the invention is particularly suited to robotic surgery techniques wherein the robotic controls can "learn" the procedure by practising on an identical replica of an anatomical region of a patient.

For example a robotic instrument could effect a "craniotomy" of precise and predetermined dimensions on a stereolithographic replica and then "learn" a surgical procedure such as implantation of electrodes for sub-cortical stimulation. The portion removed from the replica of the skull could then be used to pre-prepare a cranioplasty of slightly larger peripheral dimensions.

In a subsequent procedure on a patient, the robotic instrument could carry out the craniotomy and implantation procedures and the surgeon could then implant the pre-prepared cranioplasty with minimal manual trimming to complete the surgical procedure and the minimum of operative delay.

In addition to or as an alternative to mechanical instruments, the stereotaxy frame may also support alignable radiation emission devices for external radiotherapy procedures or for interstitial procedures. For example, interstitial hyperthermia may be conducted with a high degree of accuracy using a precisely located thermal detection device. Similarly this invention permits precise location of radiation emission devices for interstitial radiotherapy.

It will be readily apparent to a skilled addressee that many modifications and variations may be made to the various aspects of the invention without departing from the spirit and scope thereof.

I claim:

1. A method for stereotactic surgical procedures comprising the steps of:

securing, to a predetermined region of anatomy of a patient, at least two stereotaxy frame attachment means;

tomographically scanning said predetermined region to generate scanning data relating to internal and/or external surfaces of said anatomical region including said frame attachment means and inputting into a data storage means said scanning data;

computing said scanning data according to a predetermined algorithm to generate a three dimensional coordinate data set for the anatomical region;

generating from said three dimensional coordinate data set an anatomical replica of selected portions of said anatomical region including said frame attachment means;

attaching to replicated frame attachment means on said anatomical replica a stereotaxy frame and aligning instrument support means associated with said frame for carrying out a predetermined surgical procedure on a selected portion of anatomical region represented by a replication of said selected portion; and securing said stereotaxy frame to said at least two attachment means associated with said predetermined anatomical region of said patient and performing a surgical procedure on said selected portion of said anatomical region with pre-aligned instruments supported on said instrument support means.

2. A method as claimed in claim 1 wherein said frame attachment means are comprised of a material detectable by tomography scanning apparatus but otherwise do not interfere with image data produced thereby
said attachment means comprise nonmagnetic material.

3. A method as claimed in claim 2 wherein the attachment means comprise metallic or non metallic elements such as ceramics, carbon fibre, plastics, or aluminium.

4. A method as claimed in claim 3 wherein the attachment means comprises pins, plugs, sockets, spigots, or clamps for releasable attachment of said stereotaxy frame to an anatomical region in a spatially reproducible manner.

5. A method as claimed in claim 4 wherein the attachment means comprises at least two attachment elements.

6. A method as claimed in claim 5 wherein the attachment means comprises identical or non identical elements.

7. A method as in claim 1 wherein tomographic scanning is carried out with any suitable means for generation of scanning data.

8. A method as in claim 7 wherein tomographic scanning is unimodal.

9. A method as in claim 7 wherein tomographic scanning is multi-modal to generate a plurality of separate scanning data sets and/or combined scanning data sets.

10. A method as in claim 1 wherein the anatomical replica produced from scanning data is produced by stereolithographic modelling.

11. A stereotaxy frame for the method of claim 1, said stereotaxy frame comprising:

a base member having at least two spaced apertures for attachment to a region of anatomical pathology and/or a replicated region of anatomical pathology; and, an instrument support means adapted to align a trajectory of said instrument according to a selected set of spatial coordinates.

12. A stereotaxy frame according to claim 11 wherein the base member comprises two or more leg members, each having an attachment aperture at a free end thereof.

13. A stereotaxy frame according to claim 12 wherein the instrument support means is pivotally associated with said base member.

14. A stereotaxy frame according to claim 13 wherein said instrument support means comprises locking means to releasably secure said support means relative to said base member.

15. A stereotaxy frame according to claim 12 wherein is the instrument support means is pivotally associated with said base member by a ball and socket joint.

16. A stereotaxy frame according to claim 11 wherein the base member comprises a contoured member having a support surface complementary to a selected region of anatomical pathology and a tubular instrument support means fixed relative thereto.

17. A stereotaxy frame according to claim 16 wherein the contoured member comprises a moulded plastics member having a tubular instrument guide encapsulated therein.

18. A stereotaxy frame according to claim 17 wherein the contoured member includes a plurality of tubular instrument guides.

* * * * *

UNITED STATES PATENT AND TRADEMARK OFFICE
CERTIFICATE OF CORRECTION

PATENT NO. : 5,752,962
DATED : May 19, 1998
INVENTOR(S) : D'Urso

It is certified that error appears in the above-indentified patent and that said Letters Patent is hereby corrected as shown below:

Col. 8, line 62, delete "10.25 mm" and insert therefor --1.25 mm--.

Col. 10, line 6, delete "hepo" and insert therefor --head--.

Signed and Sealed this

Twenty-seventh Day of October, 1998

Attest:

BRUCE LEHMAN

*Attesting Officer*  *Commissioner of Patents and Trademarks*